(12) United States Patent
Toyoshima et al.

(10) Patent No.: US 9,321,998 B2
(45) Date of Patent: Apr. 26, 2016

(54) METHOD OF PREPARING REGENERATED HAIR FOLLICLE GERM FOR TRANSPLANTATION IN WHICH HAIR COLOR IS CONTROLLED, COMPOSITION INCLUDING REGENERATED HAIR FOLLICLE GERM FOR TRANSPLANTATION, AND METHOD OF TRANSPLANTING REGENERATED HAIR FOLLICLE GERM

(75) Inventors: Koh-ei Toyoshima, Chiba (JP); Takashi Tsuji, Chiba (JP)

(73) Assignee: Organ Technologies Inc., Tokyo (JP)

( * ) Notice: Subject to any disclaimer, the term of this patent is extended or adjusted under 35 U.S.C. 154(b) by 256 days.

(21) Appl. No.: 14/000,939

(22) PCT Filed: Feb. 21, 2012

(86) PCT No.: PCT/JP2012/054055
§ 371 (c)(1),
(2), (4) Date: Nov. 4, 2013

(87) PCT Pub. No.: WO2012/115079
PCT Pub. Date: Aug. 30, 2012

(65) Prior Publication Data
US 2014/0052167 A1    Feb. 20, 2014

(30) Foreign Application Priority Data
Feb. 24, 2011   (JP) .................................. 2011-038777

(51) Int. Cl.
*C12N 5/071* (2010.01)
*C12N 5/074* (2010.01)
*A61L 27/38* (2006.01)

(52) U.S. Cl.
CPC ........... *C12N 5/0697* (2013.01); *A61L 27/3813* (2013.01); *A61L 27/3834* (2013.01); *A61L 27/3886* (2013.01); *A61L 27/3891* (2013.01); *A61L 2430/18* (2013.01); *C12N 2506/092* (2013.01); *C12N 2506/1376* (2013.01)

(58) Field of Classification Search
None
See application file for complete search history.

(56) References Cited

U.S. PATENT DOCUMENTS

| 2004/0068284 | A1* | 4/2004 | Barrows ................... A61F 2/10 606/187 |
|---|---|---|---|
| 2004/0247572 | A1 | 12/2004 | Ideta et al. |
| 2008/0109915 | A1 | 5/2008 | Ideta et al. |
| 2008/0311044 | A1 | 12/2008 | Zheng et al. |
| 2009/0198336 | A1 | 8/2009 | Qiao et al. |
| 2010/0021866 | A1 | 1/2010 | Tsuji et al. |

FOREIGN PATENT DOCUMENTS

| JP | 2008-029756 A | 2/2008 |
|---|---|---|
| JP | 2008-029757 A | 2/2008 |
| JP | 2008-200033 A | 9/2008 |
| JP | 2008-206500 A | 9/2008 |
| JP | 2009-035514 A | 2/2009 |
| JP | 2009-529886 A | 8/2009 |
| WO | 03/022043 A1 | 3/2003 |
| WO | 2004/113514 A1 | 12/2004 |
| WO | 2006/129672 A1 | 12/2006 |
| WO | 2009/118283 A1 | 10/2009 |

OTHER PUBLICATIONS

Extended European Search Report dated Nov. 3, 2014, issued by the European Patent Office in related European Application No. EP-12749896.2 (8 pages).
Eckert, Richard Leon, et al., "Molecular Biology of Keratinocyte Differentiation"; Environmental Health Perspectives, vol. 80, Mar. 1, 1989; XP-002402480, ISSN: 0091-06765, DOI: 10.2307/3430736; pp. 109-116.
International Search Report issued in PCT/JP2012/054055 mailed on May 29, 2012 (6 pages).
English translation of the International Preliminary Report on Patentablility and Written Opinion dated Aug. 27, 2013, issued by the International Bureau of WIPO, in related International Application No. PCT/JP2012/054055 (8 pages).
Asakawa, Kyosuke, et al., "Moho Saisei ni yoru Mohatsu no Kinoteki Saisei II Seitai Mouse Hohohige Moho Yurai Saibo o Mochiita Saisei Moho Genki Ishoku ni yoru Ke no Saisei"; Regenerative Medicine, vol. 10; Feb. 1, 2011; 2P-142; p. 276.
Tanimura, Shintaro, et al., "Hair Follicle Stem Cells Provide a Functional Niche for Melanocyte Stem Cells"; Cell Stem Cell, vol. 8, No. 2, Feb. 4, 2011; pp. 177-187.
Nishimura, Emi, "Seimei no stem no Saihakken Kan Saibo System no Iji to Seigyo Stem Cell Aging kara Mietekuru Soshiki no Roka Mechanism"; Experimental Medicine, vol. 29, No. 1, Jan. 2011; pp. 29-34.
Toyoshima, Koei, et l, "Kikan Genkiho ni yoru Mohatsu no Saisei I Saikosei Moho Genki no Hinai Ishoku ni yoru Mohatsu Saisei"; Regenerative Medicine, vol. 10, 2P-141; Feb. 1, 2011; p. 276.
Toyoshima, Koei, et al., "Functional Regeneration of Hair Follicle (III), Hair color control through Regeneration of Pigmented Stem Cell Niche"; The Molecular Biology Society of Japan, Annual Program, Abstract (Web), vol. 34th, 1T1OPII-4 (1P-0308); Dec. 2011; with English translation (5 pages).
Toki, Hiroshi, et al., "Functional Regeneration of Hair through Hair Follicle Regeneration III, Hair Cycle Analysis of Regenerated Hair"; Regenerative Medicine, The Japanese Society for Regenerative Medicine, vol. 10, Suppl. 2011, 2P-143; Feb. 14, 2011; with English translation (3 pages).

(Continued)

*Primary Examiner* — Allison Fox
(74) *Attorney, Agent, or Firm* — Osha Liang LLP

(57) ABSTRACT

A method for producing a regenerative hair follicle germ for transplantation, in which a color of hair that grows after transplantation is controlled, includes preparing a first cell mass containing mesenchymal cells; preparing a second cell mass containing epithelial cells; preparing a cell mass containing pigment stem cells; binding the cell mass containing the pigment stem cells to at least one among the first cell mass and the second cell mass, and closely contacting the first cell mass and the second cell mass, at least one of which has been bound to the cell mass containing the pigment stem cells, and culturing them within a support.

17 Claims, 5 Drawing Sheets

(56) References Cited

OTHER PUBLICATIONS

Sharpe, Paul T., et al., Test-Tube Teeth; 2005 Scientific American, Inc. 293; pp. 34-41.

Reynolds, Amanda J., et al., "Trans-gender induction of hair follicles"; Nature, vol. 402, Nov. 4, 1999; pp. 33-34.

Espacenet English Abstract for WO 03-022043, published Mar. 20, 2003 (1 page).

Espacenet English Abstract for JP 2009-529886, published Aug. 27, 2009 (1 page).

Espacenet English Abstract for JP 2009-035514, published Feb. 19, 2009 (2 page).

Espacenet English Abstract for JP 2008-029756, published Feb. 14, 2008 (1 page).

Espacenet English Abstract for JP 2008-206500, published Sep. 11, 2008 (1 page).

Espacenet English Abstract for JP 2008-200033, published Sep. 4, 2008 (2 pages).

Espacenet English Abstract for JP 2008-029757, published Feb. 14, 2008 (2 pages).

\* cited by examiner

Scale Bars, 10 μm

METHOD OF PREPARING REGENERATED HAIR FOLLICLE GERM FOR TRANSPLANTATION IN WHICH HAIR COLOR IS CONTROLLED, COMPOSITION INCLUDING REGENERATED HAIR FOLLICLE GERM FOR TRANSPLANTATION, AND METHOD OF TRANSPLANTING REGENERATED HAIR FOLLICLE GERM

CROSS REFERENCE TO RELATED APPLICATION

This application is a national stage application of PCT/JP2012/054055, filed on Feb. 21, 2012, which claims the priority of Japanese application No. 2011-038777, filed on Feb. 24, 2011. This application claims the benefit and priority of these prior applications and incorporates the contents of these prior applications by reference in their entirety.

TECHNICAL FIELD

The present invention is related to a method for producing a regenerative (bioengineered) hair follicle germ (primordium) for transplantation in which hair color is controlled, a composition including the regenerative hair follicle germ for transplantation, and a method for transplanting the regenerative hair follicle germ for transplantation.

BACKGROUND ART

Regenerative medicine, in which a body part or organ which has been rendered dysfunctional due to various diseases or traumatic injuries is replaced with a regenerated body part or organ, is showing promise as a next-generation medical technique to complement medical transplantation (Non-Patent Literature 1). In past research of regenerative medicine, advances have been made in stem cell transplantation therapy in which stem cells or precursor cells are transplanted into an injured tissue or a partially dysfunctional organ to restore its function.

In regeneration of two-dimensional tissue consisting of a single type of cells such as skin or corneal epithelial cells, cardiac muscle cells, a tissue regeneration technology in which cells are organized by culturing the cells in a sheet form using cell sheet technology is nearing practical application. Therein, it is now possible to regenerate a functional skin tissue by stratifying fibroblasts, which are mesenchymal cells, and skin epidermal cells to artificially reproduce a histologically-appropriate layer structure, and this technique has been clinically applied in the treatment of severe burns.

Meanwhile, it is known that in an organ, multiple types of functional cells take on a three-dimensional arrangement to express a unique function. Almost all organs are generated by interactions between epithelial cells and mesenchymal cells during the fetal period, and exhibit unique morphology and organ functions. In current regenerative medicine techniques, it is difficult to arrange multiple types of cells in a three-dimensional fashion, and a regenerative organ construct that can immediately function ex vivo has yet to be developed.

Recently, research is being conducted with the goal of organ regeneration by regenerating an organ germ and reproducing its developmental process for ectodermal appendages such as teeth and salivary glands and skin appendages such as hair follicles. These organs are not directly related to the maintenance of life, but they are known to fall into organ loss or dysfunction. As an example, mention may be made of tooth loss due to dental caries, injury, and tooth germ hypoplasia, salivary secretion disorder associated with aging, and hair loss due to male pattern baldness and hair follicular dysplasia. These kinds of organ loss or dysfunction have a large impact on QOL (quality of life), and thus high expectations have been placed on functional restoration by organ regeneration.

Generally, in mammals and birds, ectodermal skin appendages such as hair, feathers, and nails are ubiquitous in the skin and have species-specific functions such as survival and reproduction. In mammals, hair functions to retain body heat and protect against injury and ultraviolet rays. Further, in higher mammals such as primates, hair produces characteristic colors and patterns on the body surface, and this is believed to be useful in the appeal of rank and fertility within a reproductive population. Hair also produces differences in hair quality such as thickness, hardness, and color in accordance with its area or function on the body surface, and exhibits aesthetic and functional value when it exists in large numbers in a specific area. Particularly in humans, the color and quality of head hair holds social significance, and it is believed that changes thereto due to aging or illness have a large impact on an individual's QOL.

In order to establish hair follicle regeneration medical techniques sufficient for clinical application, the growth and elongation of hair in which the regenerative hair follicle has a normal tissue structure and the hair shaft is suitable for the transplantation site is necessary. Such ectodermal appendages including skin appendages such as hair are normally generated by interactions between epithelial and mesenchymal cells during the fetal period. A hair follicle, which is one kind of ectodermal appendages, repeats growth and regression (the hair cycle) over an individual's lifetime. The regeneration of a hair bulb during the growth period is known to be induced by a molecular mechanism similar to that in the nascent stage of the hair follicle organ. Also, the regeneration of a hair bulb during such hair cycle is believed to be induced by hair papilla cells, which are mesenchymal cells. In other words, in the growth period, hair follicle epithelial stem cells are differentiation induced by hair papilla cells, which are mesenchymal cells, to regenerate a hair bulb. Further, since niches of neural crest-derived stem cells exist in the bulge region and the region below the bulge region, it is believed that hair follicles keep multiple stem cell niches and function as a stem cell pool.

In the past, attempts at hair follicle regeneration have been made by regeneration of the hair follicle variable region by replacing the mesenchymal cells (hair papilla cells and dermal root sheath cells), neogenesis of the hair follicle by mesenchymal cells having hair follicle inducing ability, reconstruction of the hair follicle by epithelial/mesenchymal cells, and the like. Further, it was recently demonstrated by the present inventors that a regenerative hair follicle germ reconstructed from adult mouse whisker-derived bulge region epithelial cells and adult mouse whisker-derived cultured hair papilla cells by the organ germ method (for example, refer to Patent Literature 1) emulates normal development and can regenerate hair follicles and hair. However, when regenerating a hair follicle using a regenerative hair follicle germ derived from an adult mouse whisker, there has been a problem in that almost all of the regenerated hairs become white hairs.

CITATION LIST

Patent Literature

Patent Literature 1: PCT International Publication No. WO 2006/129672

Non-Patent Literature

Non-Patent Literature 1: Sharpe P T, Young C S. Test-tube teeth. Sc. Am. 293, 34-41, 2005

SUMMARY OF INVENTION

Technical Problem

As described above, there have yet to be any reports so far regarding a hair follicle regeneration technique sufficient for clinical application, and particularly a hair follicle regeneration technique in which the hair color is controlled. In particular, when applying hair regeneration techniques in humans, it is necessary to obtain regenerative hair in which the hair color is controlled from an adult-derived tissue, and thus a method for controlling the hair color of an adult tissue-derived regenerative hair has been strongly desired.

Solution to Problem

In order to solve the above-described problem, the present inventors first focused on the distribution and distribution regions of melanoblasts, which are the cells responsible for hair color, and analyzed the function of the cells that exist in each distribution region. The present inventors thereby discovered a method for producing a regenerative hair follicle germ for transplantation in which the hair color is controlled by applying the function of the cells included in the melanoblast distribution regions.

Namely, the present invention is a method for producing a regenerative hair follicle germ for transplantation in which a color of hair that grows after transplantation is controlled, comprising: preparing a first cell mass comprising mesenchymal cells, preparing a second cell mass comprising epithelial cells, preparing a cell mass comprising pigment stem cells, binding the cell mass comprising the pigment stem cells to at least one among the first cell mass and the second cell mass, and subsequently closely contacting the first cell mass and the second cell mass, at least one of which has been bound to the cell mass comprising the pigment stem cells, and culturing them within a support.

Herein, in one embodiment of the method for producing a regenerative hair follicle germ for transplantation of the present invention, the first cell mass substantially consists of mesenchymal cells.

In addition, in one embodiment of the method for producing a regenerative hair follicle germ for transplantation of the present invention, the second cell mass substantially consists of epithelial cells.

In addition, in one embodiment of the method for producing a regenerative hair follicle germ for transplantation of the present invention, the cell mass comprising the pigment stem cells is subjected to a unification treatment.

In addition, in one embodiment of the method for producing a regenerative hair follicle germ for transplantation of the present invention, the pigment stem cells are subbulge region-derived melanoblasts or hair matrix base-derived melanocyte precursor cells.

In addition, in one embodiment of the method for producing a regenerative hair follicle germ for transplantation of the present invention, when binding the cell masses together, the ratio of the number of cells in the first cell mass or the number of cells in the second cell mass relative to the number of cells in the cell mass comprising the pigment stem cells is within a range of 0.1:1 to 100:1.

In addition, in one embodiment of the method for producing a regenerative hair follicle germ for transplantation of the present invention, the mesenchymal cells are hair papilla cells or dermal root sheath cells.

In addition, in one embodiment of the method for producing a regenerative hair follicle germ for transplantation of the present invention, the epithelial cells are bulge region epithelial cells or hair matrix basal epithelial cells.

In addition, in one embodiment of the method for producing a regenerative hair follicle germ for transplantation of the present invention, the mesenchymal cells or the epithelial cells are derived from an adult hair follicle.

In addition, in one embodiment of the method for producing a regenerative hair follicle germ for transplantation of the present invention, the method further comprises inserting a guide into the regenerative hair follicle germ.

In addition, in one embodiment of the method for producing a regenerative hair follicle germ for transplantation of the present invention, a regenerative hair follicle that is regenerated upon transplanting the regenerative hair follicle germ comprises a melanoblast stem cell niche.

In addition, in one embodiment of the method for producing a regenerative hair follicle germ for transplantation of the present invention, a regenerative hair follicle that is regenerated upon transplanting the regenerative hair follicle germ is capable of permanently forming colored hair.

Another embodiment of the present invention is related to a composition comprising a regenerative hair follicle germ for transplantation in which the hair color is controlled that is produced by the above-described method for producing a regenerative hair follicle germ for transplantation.

Further, another embodiment of the present invention is related to a method for transplanting a regenerative hair follicle germ for transplantation in which the hair color is controlled comprising: transplanting a regenerative hair follicle germ for transplantation that is produced by the above-described method for producing a regenerative hair follicle germ for transplantation into a target site.

Also, in one embodiment of the method for transplanting a regenerative hair follicle germ for transplantation of the present invention, a portion on the epithelial cell side of the transplanted regenerative hair follicle germ and the epithelial cells of the target elongate and connect along the guide by maintaining the guide in a state in which it protrudes from a transplant site.

Effects of the Invention

According to the present invention, a regenerative hair follicle germ for transplantation in which hair that grows first after transplantation is colored hair can be produced by using pigment stem cells prepared separately from the epithelial cells or mesenchymal cells during production of the regenerative hair follicle germ. Further, the regenerative hair follicle germ for transplantation produced by the present invention can regenerate hair having not only hair color but also a normal hair shaft.

In addition, in one embodiment of the present invention, a melanoblast stem cell niche can be formed in a regenerative hair follicle that is regenerated after transplantation of a regenerative hair follicle germ for transplantation produced by the present invention. Thereby, the melanoblast stem cell niche in the hair follicle can maintain the melanoblasts and appropriately provide melanocytes, and thus colored hair can be formed over a long period of time.

BRIEF DESCRIPTION OF DRAWINGS

In FIG. 1, DP indicates a hair (dermal) papilla, and SG indicates a sebaceous gland.

FIG. 2a shows a hair growth site upon transplanting a regenerative hair follicle germ produced from adult mouse side whisker-derived bulge region epithelial cells and adult mouse side whisker-derived hair papilla cells (control). Also, FIG. 2b shows a hair growth site upon transplanting a regenerative hair follicle germ produced by further adding adult mouse side whisker-derived subbulge region cells to adult mouse side whisker-derived bulge region epithelial cells and adult mouse side whisker-derived hair papilla cells (subbulge addition segment). FIG. 2c shows a hair growth site upon transplanting a regenerative hair follicle germ produced by further adding cells collected from an adult mouse side whisker-derived hair matrix base to adult mouse side whisker-derived bulge region epithelial cells and adult mouse side whisker-derived hair papilla cells (hair matrix base addition segment). White hair was obtained in the control (FIG. 2a), whereas black hair was able to be obtained in the subbulge addition segment and the hair matrix base addition segment (black arrow mark in FIG. 2b and FIG. 2c). The white arrow mark in FIG. 2b indicates a white regenerative hair.

FIG. 3A shows an image of a natural hair follicle having black hair, FIG. 3B shows an image of a hair follicle having white hair derived from a regenerative hair follicle germ produced from adult mouse side whisker-derived bulge region epithelial cells and adult mouse side whisker-derived hair papilla cells, and FIG. 3C shows an image of a hair follicle having black hair derived from a regenerative hair follicle germ produced by adding adult mouse side whisker-derived subbulge region cells (subbulge addition segment) to adult mouse side whisker-derived bulge region epithelial cells and adult mouse side whisker-derived hair papilla cells. The arrow marks in FIG. 3 indicate areas of dopachrome tautomerase detection.

DESCRIPTION OF EMBODIMENTS

Figure 1:
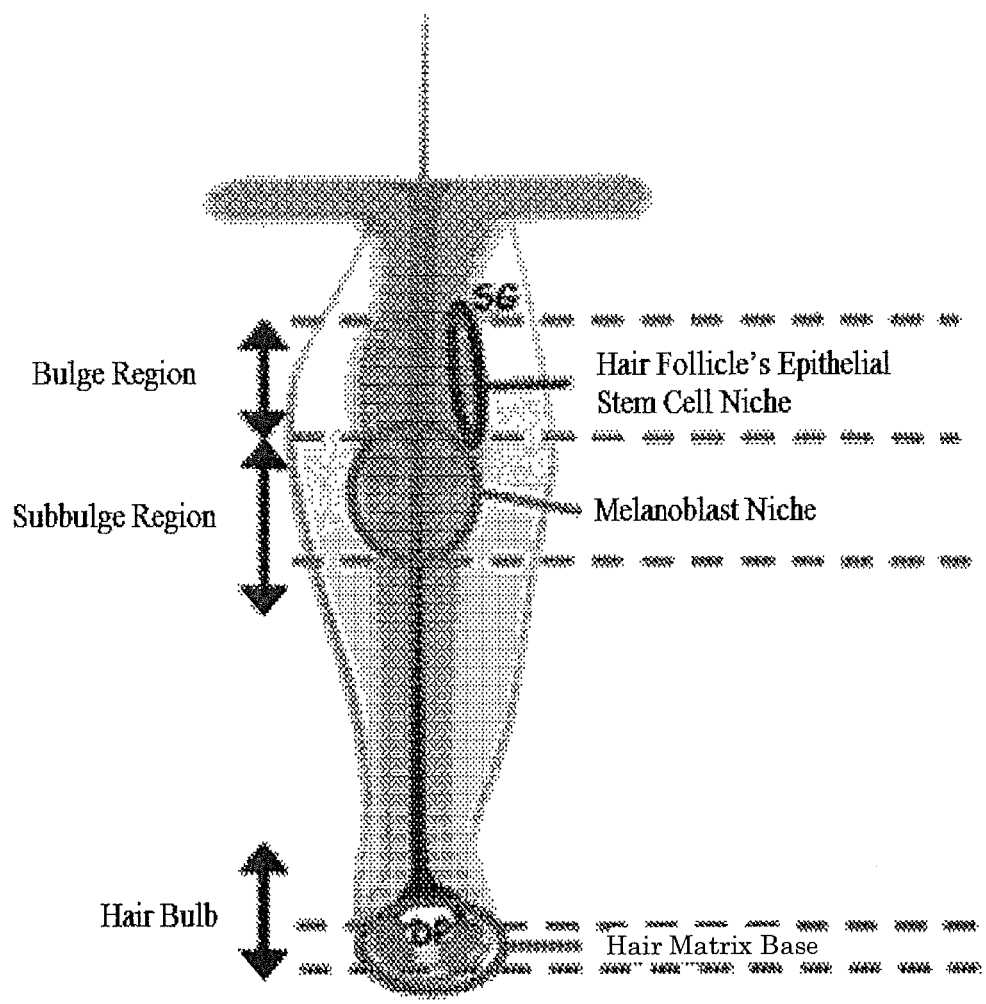
FIG. 1 is a schematic view illustrating the distribution of melanoblasts and melanocyte precursor cells in a hair follicle. A melanoblast niche in which melanoblasts are distributed exists in a subbulge region of the hair follicle, and melanocyte precursor cells are distributed in a hair matrix base.

A first embodiment of the production method according to the present invention is a method for producing a regenerative hair follicle germ for transplantation in which a color of hair that grows after transplantation is controlled, comprising: preparing a first cell mass comprising mesenchymal cells, preparing a second cell mass comprising epithelial cells, preparing a cell mass comprising pigment stem cells, binding the cell mass comprising the pigment stem cells to at least one among the first cell mass and the second cell mass, and subsequently closely contacting the first cell mass and the second cell mass, at least one of which has been bound to the cell mass comprising the pigment stem cells, and culturing them within a support.

In the present specification, "mesenchymal cells" indicate cells derived from a mesenchymal tissue and cells obtained by culturing such mesenchymal tissue-derived cells, and "epithelial cells" indicate cells derived from an epithelial tissue and cells obtained by culturing such epithelial tissue-derived cells.

Pigment cells are cells that are distributed within the epidermal layer and dermal layer of skin and within the epithelial layer of hair follicles and produce melanin. The melanin produced by pigment cells is deeply involved in a color of hair. Also, pigment cells are known to differentiate from pigment stem cells or precursor cells of pigment cells.

Also, in the present specification, "pigment stem cells" indicate melanocyte precursor cells and melanoblasts (pigment stem cells) that differentiate into pigment cells (melanocytes). When pigment stem cells are included, one type of the above-mentioned cells can be used, and a mixture of both types can also be used. In addition, melanoblasts indicate stem cells in an undifferentiated state that do not have pigment and can differentiate into melanocytes and melanocyte precursor cells. Melanoblasts are maintained in an undifferentiated state over a long period of time in a specific stem cell niche in a hair follicle. Further, melanocyte precursor cells indicate precursor cells in an undifferentiated state that do not have pigment and can differentiate into melanocytes. Also, pigment cells (melanocytes) indicate terminally-differentiated cells that have pigment.

Also, in the present specification, "a cell mass comprising pigment stem cells" includes a tissue or region comprising pigment stem cells such as the above-described pigment stem cells, cells in a state in which such a tissue or region has been isolated into cellular units by an enzyme treatment or unification treatment or the like, or a cell aggregate obtained by centrifugal separation or the like of such isolated cells. Further, a cell mass comprising pigment stem cells can be a cell mass substantially consisting of pigment stem cells.

In addition, in the present invention, a "bulge region" indicates a hair follicle constant region that is below the sebaceous gland attachment site of the hair follicle and above the hair erector muscle attachment site. In the case of a mouse side whisker or the like in which hair erector muscles do not exist, a ringwurst exists in an area corresponding to the hair erector muscle attachment site. A ringwurst is a ring-shaped structure consisting of neural crest-derived mesenchymal cells attached to the bottommost end of a side whisker hair follicle invariant region, and this structure is characteristic of rodent side whiskers. Therefore, in the present specification, the "bulge region" in a hair follicle of a side whisker or the like in which hair erector muscles do not exist indicates a region that is below the sebaceous gland attachment site of the hair follicle and above the ringwurst. A constant region (invariant region) indicates a region in which there are no changes in the tissue structure of the hair follicle such as growth or regression associated with the hair cycle of the hair follicle. The "subbulge region" indicates a bottommost end portion of a constant region that is adjacent to the region below the bulge region.

Also, in the present invention, a "hair matrix base" indicates a region that is positioned below the Auber's line in the hair matrix of a hair bulb, in which melanocytes that produce melanin are not distributed.

In the present specification, a "regenerative hair follicle" means a hair follicle germ produced by a method comprising: closely contacting a first cell mass comprising mesenchymal cells and a second cell mass comprising epithelial cells and culturing them within a support.

The step for "closely contacting a first cell mass comprising mesenchymal cells and a second cell mass comprising epithelial cells and culturing them within a support" is described in, for example, Patent Literature 1, Japanese Unexamined Patent Application, First Publication No. 2008-29756, Japanese Unexamined Patent Application, First Publication No. 2008-206500, Japanese Unexamined Patent Application, First Publication No. 2008-200033, and Japanese Unexamined Patent Application, First Publication No. 2008-29757. The descriptions of each of these documents are incorporated in their entirety for reference into the present specification.

At least one of the first cell mass and the second cell mass is bound to the cell mass comprising the pigment stem cells. Subsequently, this cell mass is cultured within a support together with the other cell mass to produce a regenerative hair follicle germ. Therein, the cell mass comprising the pigment stem cells can be bound to either of the first cell mass and the second cell mass, or the cell mass comprising the pigment stem cells can be bound to both of the first cell mass and the second cell mass.

Since melanoblasts exist in the epithelial layer of a hair follicle, when using melanoblasts as pigment stem cells, it is preferable to bind cell mass comprising melanoblasts to cell mass comprising epithelial cells because the function of the stem cells can be maintained.

In the present specification, "binding the first or second cell mass and the cell mass comprising pigment stem cells" includes entirely or partially mixing one cell mass with another cell mass, and also includes contacting or adhering the surfaces of the cell masses to each other. Therefore, the first or second cell mass which has been bound to the cell mass comprising the pigment stem cells is in a state in which the pigment stem cells have been mixed or incorporated into the cell mass.

When binding the cell mass comprising the pigment stem cells to at least one of the first cell mass and the second cell mass, the ratio of the number of cells in the first cell mass or the number of cells in the second cell mass relative to the number of cells in the cell mass comprising the pigment stem cells can be appropriately set depending on conditions such as the cells to be used. However, for example, the ratio is preferably adjusted to be within a range of 0.1:1 to 100:1, more preferably adjusted to be within a range of 0.1:1 to 10:1, and further more preferably adjusted to be within a range of 0.5:1 to 2:1.

However, the ratio of the number of cells in the first cell mass or the number of cells in the second cell mass relative to the number of cells in the cell mass comprising the pigment stem cells is not limited to the ranges described above as long as the hair color of the regenerative hair follicle germ that is produced can be controlled.

When the cell mass comprising the pigment stem cells is bound to both the first cell mass and the second cell mass, the cell mass comprising the pigment stem cells can be bound so that the above-described ranges are satisfied relative to each of the first and second cell masses.

Further, at this time, the shade of the hair color can also be controlled by adjusting the proportion of the number of the pigment stem cells that are bound to the first cell mass or the second cell mass.

Also, when closely contacting the first cell mass and the second cell mass after binding the cell mass comprising the pigment stem cells and culturing them in a support, the ratio of the number of cells in the cell mass comprising mesenchymal cells relative to the number of cells in the cell mass comprising epithelial cells can be appropriately set depending on conditions such as the cells to be used. However, for example, the ratio is preferably adjusted to be within a range of 0.1:1 to 3:1, and more preferably adjusted to be within a range of 0.3:1 to 1:1. During the culture, it is preferable to raise the proportion of the number of epithelial cells because this enables the growth rate and hair quality of regenerative hair to be improved.

Further, when incorporating pigment stem cells into one of the first cell mass and the second cell mass, the other cell mass can substantially consist of only mesenchymal cells or only epithelial cells. In the present invention, the phrase "substantially consists of only mesenchymal cells" means that the cell mass performs a function identical to a cell mass that consists of only mesenchymal cells. It preferably indicates a state in which the cell mass does not include anything other than cells which are mesenchymal cells as far as possible. Also, the cell mass can include cells of different types as long as they are mesenchymal cells. The same applies to the phrase "substantially consists of only epithelial cells".

Herein, a cell mass can be in a state in which the cells are closely adhered or not closely adhered, and it may be a tissue, or a group of cells which has been subjected to a unification treatment after collection from a tissue, or a cell aggregate prepared from discrete cells. The use of a tissue is advantageous because it is easy to obtain an organ with correct cell arrangement and shape, but there may be constraints on the amount that can be obtained. Cultured cells can also be used to prepare a cell aggregate, and a cell aggregate is relatively easy to obtain when using cultured cells, making cultured cells preferable at least from this perspective. When injecting the cell masses into a support and closely contacting and then culturing them in order to produce a regenerative hair follicle germ, the cell masses are preferably tissues or cell aggregates in which the cells are closely adhered.

As the pigment stem cells used in the present invention, it is preferable to use pigment stem cells derived from a hair follicle because this facilitates the orientation to hair follicle regeneration. For example, when melanoblasts are used as the pigment stem cells, melanoblasts that exist in the subbulge region of a hair follicle can be used, and when using melanocyte precursor cells as the pigment stem cells, melanocyte precursor cells that exist in the hair matrix base of a hair follicle can be used.

Also, as pigment stem cells that are derived from somewhere other than a hair follicle, cells which are distributed in the epidermal layer in the skin can be used.

At least one of the mesenchymal cells and the epithelial cells used in the present invention is preferably derived from a hair follicle (including an organ, tissue, and cells that constitute a hair follicle). Thereby, an organ can be easily formed using cells which are already oriented to the hair follicle. Further, in order to produce a hair follicle more reliably, it is most preferable for both the mesenchymal cells and the epithelial cells to be derived from a hair follicle.

In other words, when producing a regenerative hair follicle germ, hair follicle-derived mesenchymal cells or epithelial cells can be used. More specifically, hair papilla cells, dermal root sheath cells, nascent skin mesenchymal cells, and the like can be used as the mesenchymal cells, and external root sheath outermost layer cells of the bulge region, hair matrix basal epithelial cells, and the like can be used as the epithelial cells. In addition, hair follicle mesenchymal cells induced from an iPS cell or an ES cell can also be used as the mesenchymal cells, and hair follicle epithelial cells induced from an iPS cell or an ES cell can also be used as the epithelial cells.

In addition, a hair follicle for collecting mesenchymal cells, epithelial cells, and pigment stem cells is preferably in the growth stage. By using cells derived from a hair follicle in the growth stage, it is possible to induce high-quality regenerative hair at high frequency. Also, the hair follicle can be derived from an embryo or an adult. Collecting cells from an embryo-derived hair follicle is preferable because hair follicle cells in the nascent stage of the hair follicle organ can be efficiently collected and undifferentiated cells can be obtained. On the other hand, collecting cells from an adult-derived hair follicle is preferable because useful cells can be isolated and obtained utilizing the regionality of the cell distribution in an organ. In particular, for clinical application of the present invention in humans, cells of the subject can be utilized and this is preferable with respect to avoiding immunologic transplant rejection and avoiding ethical problems such as using an ES cell. Furthermore, there have been reports that a hair follicle after transplantation is immunologically tolerated (Reynolds et. al., Trans-gender induction of hair follicles. Nature. 1999 Nov 4; 402 (6757): 33-4). Alternatively, if immune suppression is possible by other methods, surgical materials and the like derived from an adult of another family produced by cosmetic plastic surgery or the like can be used, and this is preferable given its extremely high value for industrial application.

Cells derived from other mesenchymal tissue in vivo can also be used as mesenchymal cells derived from somewhere other than a hair follicle. Preferably, such cells are bone marrow cells or mesenchymal cells that do not include blood cells, and further preferably mesenchymal cells from within the oral cavity, bone marrow cells from within the jaw bone, mesenchymal cells derived from cranial neural crest cells, mesenchymal precursor cells or stem cells thereof that can differentiate into such mesenchymal cells, and the like. Japanese Unexamined Patent Application, First Publication No. 2008-206500 describes an example in which amnion-derived cells are used as the mesenchymal cells, and Japanese Unexamined Patent Application, First Publication No. 2008-200033 describes an example in which cells obtained by differentiation induction of totipotent stem cells are used as the mesenchymal cells. The descriptions in these publications are incorporated in their entirety for reference into the present specification.

Cells derived from other epithelial tissue in vivo can also be used as epithelial cells derived from somewhere other than a hair follicle. Preferably, such cells are epithelial cells of skin, mucous membranes within oral cavity or gums, and further preferably immature epithelial precursor cells, for example non-keratinized epithelial cells or stem cells thereof, or the like that can differentiate into epithelial cells such as skin or mucous membranes or the like which have differentiated, e.g. keratinized, or parakeratinized. Japanese Unexamined Patent Application, First Publication No. 2008-29756 describes an example in which oral cavity epithelial cells or primary cultured cells thereof are used as the epithelial cells, and the descriptions therein are incorporated in their entirety for reference into the present specification. From the perspective of the use of an autogenous tissue, it is preferable to use mesenchymal cells and epithelial cells or a tissue including these cells from the target of transplantation.

The mesenchymal cells, epithelial cells, pigment stem cells, or a tissue including these cells for producing the regenerative hair follicle germ can be collected from mammals such as primates (e.g. humans, monkeys, etc.) and ungulates (e.g. pigs, cows, horses, etc.), small mammals such as rodents (e.g. mice, rats, rabbits, etc.), as well as various other animals such as dogs and cats. The collection of mesenchymal cells, epithelial cells, pigment stem cells, or a tissue including these cells should be carried out by extracting under aseptic conditions and storing in an appropriate storage solution, while applying the conditions normally used for a tissue collection without change.

The mesenchymal cells and epithelial cells from a hair follicle are prepared by, for example, first separating the hair follicle which has been isolated from a surrounding tissue into its mesenchymal tissue and epithelial tissue in accordance with its shape.

Further, in the preparation of pigment stem cells from a hair follicle, for example, when isolating the subbulge region including melanoblasts, it can be isolated as the bottommost end of a constant region that is adjacent to the bulge region using the sebaceous glands and hair erector muscles under microscopic observation as markers. Also, when isolating a hair matrix base including melanocyte precursor cells, it can be isolated from the bottommost end of a variable region below the Auber's line using the hair bulb of the hair papilla under microscopic observation as a marker. In addition, when using cells derived from an animal or cultured cells in which a gene into which GFP has been incorporated under a Dct promoter, which is a marker of melanoblasts, has been introduced as a material, melanoblasts can be further isolated/acquired using a cell sorter from cells which have been unified by an enzyme treatment. Also, when isolating mesenchymal cells, epithelial cells, a subbulge region, a hair matrix base, and the like from a tissue, an enzyme can be used to facilitate the isolation. As the enzyme, mention may be made of known enzymes such as dispase, collagenase, and trypsin, and those skilled in the art can use an appropriate enzyme of their choice.

Further, a cell mass including mesenchymal cells, epithelial cells, or pigment stem cells isolated from a hair follicle is preferably subjected to a unification treatment by passage through a filter for cell segregation before it is used in the production of a regenerative hair follicle germ. A unification treatment involves releasing the adhesion between cells to impart them with fluidity, and this treatment is preferably carried out because it enables added cells to be uniformly mixed and enables cells to be handled with a micropipette when producing a regenerative hair follicle germ. The filter for cell segregation is not particularly limited as long as it can segregate a cell mass including mesenchymal cells, epithelial cells, or pigment stem cells from other tissue and other cells. The diameter of the filter for cell segregation can be appropriately selected by a person skilled in the art for each cell to be collected. For example, a filter having a diameter of 40 μm to 100 μm can be used.

A cell aggregate in the present invention means an aggregation of cells derived from a mesenchymal tissue or an epithelial tissue, an aggregation of a cell group containing pigment stem cells, or an aggregation of a cell group containing cells derived from a mesenchymal tissue or an epithelial tissue and pigment stem cells, and the like. Such a cell aggregate can be prepared by, for example, aggregating cells obtained by dispersing a mesenchymal tissue, an epithelial tissue, or a region containing pigment stem cells into discrete cells or aggregating cells obtained by primary culture or subculture of such cells.

In order to disperse cells, an enzyme such as dispase, collagenase, and trypsin can be used. When performing a primary culture or subculture of dispersed cells before preparing a cell aggregate in order to obtain a sufficient number of cells, a medium that is generally used in culturing animal cells such as Dulbecco's Modified Eagle Medium (DMEM) can be used as the medium for culture. In order to promote cell growth, serum can be added, or as an alternative for serum, for example, a cell growth factor such as FGF, EGF, and PDGF or a known serum component such as transferrin can be added. When adding serum, the concentration can be appropriately modified depending on the state of the culture at the time of addition, but it can normally be set to around 10%. For the cell culture, normal culture conditions are applied, for example culture in an incubator having 5% $CO_2$ concentration at a temperature of about 37° C. Further, an antibiotic such as streptomycin can also be added as appropriate.

In order to aggregate cells, for example, a cell suspension can be centrifuged. In a cell aggregate of mesenchymal cells and epithelial cells, the respective cells are preferably in a high density state in order to ensure that the cells reliably interact with each other when they are brought into close contact. A high density state means a degree of density equivalent to that when constituting a tissue, for example $5 \times 10^7$ cells/ml to $1 \times 10^9$ cells/ml, preferably $1 \times 10^8$ cells/ml to $1 \times 10^9$ cells/ml, and most preferably $2 \times 10^8$ cells/ml to $8 \times 10^8$ cells/ml. The method for achieving high density of the cell aggregate is not particularly limited, and, for example, it can be achieved by a method in which the cells are aggregated by centrifugation and then precipitated. Centrifugation is preferred because it can easily achieve high density without compromising the activity of the cells. Centrifugation can be carried out for 3 to 10 minutes at a number of rotations that provides a centrifugal force of 300×g to 1200×g and preferably 500×g to 1000×g. If the centrifugation is less than 300×g, the cell density tends not to reach a sufficiently high level, whereas if the centrifugation is greater than 1200×g, the cells may be damaged.

When preparing a high-density cell aggregate by centrifugation, a cell suspension is normally prepared in a container such as a tube used for centrifugation of cells and then the cells are centrifuged. After centrifugation, the cells remain as a precipitate and as much of the supernatant is removed as possible. At this time, the amount of components other than the target cells (such as culture solution, buffer, etc.) is preferably equal to or less than the amount of the cells, and most preferably no components other than the target cells are included. If these kind of high-density cell masses are brought into close contact within a support carrier by a method to be explained below, the cells make tight contact with each other and cell-cell interaction is effectively exhibited.

Further, a cell aggregate containing mesenchymal cells or epithelial cells and pigment stem cells can also be prepared by, for example, a centrifugation treatment like that described above. Specifically, a cell mass comprising mesenchymal cells or epithelial cells and pigment stem cells that are included in preferred proportions, respectively, is prepared and incorporated into a cell suspension to be used for centrifugation, and such cell suspension is then centrifuged to produce a cell aggregate into which pigment stem cells are mixed.

The support carrier to be used for the purpose of culturing the first and second cell masses is not particularly limited as long as the cell culture can be carried out therein. For example, gel, fiber, and solid support carriers are preferred. By using such a support carrier, excessive pressure on the regenerative hair follicle germ in vivo can be further prevented.

As the support carrier to be used in the present invention, mention may be made of, for example, collagen, agarose gel, carboxymethyl cellulose, gelatin, agar, hydrogel, Cell Matrix (product name), Mebiol Gel (product name), Matrigel (product name), elastin, fibrin, laminin, an extracellular matrix mixture, polyglycolic acid (PGA), polylactic acid (PLA), lactic acid/glycolic acid copolymer (PLGA), and the like. Therein, collagen, agarose gel, carboxymethyl cellulose, gelatin, agar, hydrogel, Cell Matrix, Mebiol Gel, Matrigel, an extracellular matrix mixture, elastin, fibrin, and laminin, which have appropriate hardness and retentivity, are preferred.

For example, a liquid support carrier can be used and cured after disposing a regenerative hair follicle germ consisting of the first and second cell masses therein. For example, by preparing a collagen gel drop on a culture dish, disposing the regenerative hair follicle germ in the collagen drop, and then culturing within a $CO_2$ incubator at 37° C., the collagen can be gelled.

The support carrier used for the purpose of culturing the first and second cell masses preferably has a retentivity sufficient to retain the close contact state of the cell masses without dispersion of the cells. Herein, the "close contact state" means a state in which the high-density cell masses of mesenchymal cells and epithelial cells described above maintain an equally high density even near the contact surface between the mesenchymal cells and the epithelial cells. If the support carrier capable of retaining a close contact state is, for example, collagen, appropriate hardness can be provided by using the collagen at a concentration such that the final concentration is 2 mg/ml to 3 mg/ml, or in other words a concentration such that the jelly strength is 120 g to 250 g according to a method mutatis mutandis in accordance with JIS-K6503-1996 (measured as a load necessary to depress a 12.7 mm diameter plunger by 4 mm). Other types of support carriers can be preferably used as the support carrier in the present invention as long as they have equivalent strength according to an equivalent evaluation method. Also, a support carrier having a hardness corresponding to the intended jelly strength can be obtained by mixing one or more types of support carriers.

The method for disposing the first and second cell masses in the support carrier is not particularly limited. If the cell masses are cell aggregates, for example, a precipitate obtained by centrifugation as described above can be disposed by inserting it into the support carrier with a microsyringe or the like. If the cell masses are a tissue, such can be disposed at an arbitrary location in the support carrier using the tip of a syringe needle or the like.

The method for disposing the first and second cell masses in close contact in the support carrier in the present invention is not particularly limited. For example, the cell masses can be brought into close contact by disposing one of the cell masses in the support carrier and then disposing the other cell mass so that it presses against the one cell mass. More specifically, one of the cell masses can be pressed against the other cell mass by appropriately changing the position of the tip of the above syringe needle in the support carrier. When using an epithelial tissue or a mesenchymal tissue as the cell masses, it is preferable to dispose the surface of the epithelial tissue or mesenchymal tissue at which the tissue had been in contact with the mesenchymal tissue or epithelial tissue, respectively, in the original organ (including a tissue belonging to the organ) so that it contacts the other cell mass.

It is also preferable to include solidifying the support carrier after disposing the cell masses. Thereby, the cells aggregate further and a state of even higher density can be achieved. For example, when using collagen gel, it can be solidified by allowing it to stand for several minutes to several tens of minutes at the culture temperature. At this time, the fewer components other than cells there are in the cell masses, the higher the density which can be realized.

The culture duration differs depending on the number of cells disposed within the support carrier, the state of the cell masses, the culture conditions, the type of animal, and the like, and the duration can be appropriately chosen by a person skilled in the art.

By increasing the culture duration, the formation of the regenerative hair follicle germ can be further progressed. In order to obtain a desired condition, for example, the culture can be carried out for 1 day or more, 2 days or more, 6 days or more, 30 days or more, 50 days or more, 100 days or more, or 300 days or more, and the medium and culture conditions can be changed during the culture.

For example, when transplanting a regenerative hair follicle germ, in order to obtain functional hair, the regenerative hair follicle germ is preferably cultured for at least one day, and more preferably cultured for 2 or more days.

For the culture process within the support carrier, a support carrier including the first and second cell masses can be cultured alone or cultured in the presence of other animal cells or the like.

When culturing the support carrier alone, conditions which are generally used for culture of animal cells can be used as the culture conditions. Also, mammal-derived serum can be added to the culture, and various cell factors known to be effective in the proliferation or differentiation of such cells can also be added. Examples of such cell factors can include FGF, BMP, and the like.

From the perspective of gas exchange and nutrient supply to the cell masses, and from the perspective of being able to perform all steps in vitro without contact/contamination with other animal cells, the culture within the support carrier is preferably an organ culture. In an organ culture, the culture is generally carried out by floating a porous membrane on a medium suitable for animal cell growth and then placing the support carrier including the first and second cell masses on the membrane. The porous membrane used herein preferably has many pores of about 0.3 to 5 µm, and mention may be made of, for example, Cell Culture Insert (product name) and Isopore Filter (product name).

Also, according to another embodiment of the present invention, a guide can be inserted into the regenerative hair follicle germ consisting of the first and second cell masses after disposing the first and second cell masses in close contact in the support carrier or after the culture.

A "guide" which can be used in the present invention is inserted into the regenerative hair follicle germ during culture that was constructed by organ culture and facilitates connection between an epithelial cell-side portion of the regenerative hair follicle germ and the recipient-side epithelial cells after transplantation of the regenerative hair follicle germ. The guide to be used is not particularly limited as long as it has the above-mentioned effects. For example, mention may be made of a fiber made from a polymer such as nylon or a synthetic or natural bioabsorbable polymer, a metallic fiber such as stainless steel, a carbon fiber, a chemical fiber such as a glass fiber, and a natural animal or plant fiber, and the like. More specifically, mention may be made of a nylon thread, a stainless steel wire, or the like. In particular, in a regenerative hair follicle germ, hair derived from a living body can be used as the guide. Further, the guide used in the present invention can take on the form of a hollow thread. The diameter of the guide can be appropriately set by a person skilled in the art. For example, the diameter is preferably 5 to 100 µm, and more preferably 20 to 50 µm. In addition, the length of the guide used in the regenerative hair follicle germ can also be appropriately set by a person skilled in the art. For example, the length is preferably 1 to 10 mm, and more preferably 4 to 6 mm.

The guide is inserted from the epithelial cell side of the cell masses that become the regenerative hair follicle germ such that the structure of the regenerative hair follicle germ, particularly the contact surface between the first cell mass and the second cell mass, is not damaged by the insertion of the guide, and the guide vertically penetrates through the first cell mass and the second cell mass.

Also, the guide can be inserted into the cell masses that become the regenerative hair follicle germ immediately after the start of organ culture, or in other words, immediately after disposing the epithelial cells and mesenchymal cells in the medium. When inserting the guide some time after the start of culture, since the strength of the epithelial cells of the regenerative hair follicle germ increases due to cell adhesion by organ culture, the penetration of the guide can be increased by using a strong material for the guide (such as a stainless steel wire or the like) and sharpening the tip of the guide and the like, enabling the guide to be inserted 1 to 2 days after the start of culture. The guide is preferably inserted immediately after preparation of the organ germ because at this time a flexible material with low foreign-body reaction on a living body such as a nylon thread can be used. Further, inserting the guide some time after the start of culture is also preferable because the contact surface between the first cell mass and the second cell mass becomes more strongly adhered and the contact surface is not damaged by the insertion of the guide.

Further, after inserting the guide into the regenerative hair follicle germ, the regenerative hair follicle germ can be cultured in a state in which the guide has been inserted. The duration of culture after insertion of the guide is, for example, preferably 1 to 4 days, and more preferably 1.5 to 2 days. By culturing for 2 days after insertion of the guide, the adhesion between the guide and the regenerative hair follicle germ becomes strong, and this helps to prevent any deviations that may occur during transplantation. Also, culturing after the guide has been inserted is preferable because the portion on the epithelial cell side of the regenerative hair follicle germ can be elongated along the guide. This elongation can improve the efficiency and stability of the autonomous adhesion between the epithelial cell-side portion of the regenerative hair follicle germ and the epithelial cells of the recipient after transplantation of the regenerative hair follicle germ.

In one embodiment of the present invention, the regenerative hair follicle germ for transplantation produced by the method for production of the present invention is a regenerative hair follicle germ that is capable of forming a functional melanoblast stem cell niche in the hair follicle which is regenerated after transplantation. This melanoblast stem cell niche is formed in an external root sheath of the subbulge region similar to a natural hair follicle. Herein, a functional melanoblast stem cell niche indicates a stem cell niche that has a function to maintain melanoblasts and a function to differentiate/supply melanocytes in a portion that constitutes the niche. The regenerative hair follicle germ for transplantation in one embodiment of the present invention can regenerate a hair follicle comprising a functional melanoblast stem cell niche, and thus the hair follicle is capable of permanently forming colored hair.

Also, according to another embodiment of the present invention, a method is provided for transplanting a regenerative hair follicle germ for transplantation in which the hair color is controlled that is produced by the method for production of the present invention into a target site.

By transplanting the regenerative hair follicle germ for transplantation in which the hair color is controlled that is produced by the method for production of the present invention, growth of hair in which the hair color is controlled can be obtained at the transplant site. In particular, even when the regenerative hair follicle germ has been reconstructed from an adult-derived hair follicle, colored hair can be obtained at the transplant site by transplantation of the regenerative hair follicle germ.

The regenerative hair follicle germ for transplantation in which the hair color is controlled can be transplanted to a target site in accordance with methods publicly known by those skilled in the art. For example, it can be transplanted by using a hair transplant which utilizes the Shapiro hair transplant technique or a Choi hair transplant device or an implanter which utilizes air pressure or the like. The Shapiro hair transplant technique is a method in which a graft wound is created at the target transplant site using a micro scalpel or the like and then the transplant is transplanted using tweezers. When applying this kind of hair transplant technique, since the regenerative hair follicle germ for transplantation has a guide, it is possible to operate without directly touching the regenerative hair follicle germ, and the operation can be therefore easily performed.

The transplantation depth of the regenerative hair follicle germ is, for example, preferably 0.05 to 5 mm, more preferably 0.1 to 1 mm, and most preferably 0.3 to 0.5 mm. In particular, when transplanting a regenerative hair follicle germ into a recipient, there are cases in which it is preferably transplanted into the dermic layer and more preferably above the boundary surface between the dermal and subdermal tissue at which the hair follicle formation and subsequent hair growth efficiency are excellent. The regenerative hair follicle germ during transplantation is preferably transplanted so that the epithelial cell side of the regenerative hair follicle germ faces toward the body surface side of the recipient and the mesenchymal cell side of the regenerative hair follicle germ faces toward the inside of the body of the recipient, because this enables the hair growth direction to be controlled toward the body surface side. It is also preferable to adjust the transplantation depth so that the top end of the epithelial cell portion of the regenerative hair follicle germ is exposed at the top end of the graft wound because this can further increase the continuity with the epithelial cells of the recipient.

In addition, after transplantation of the regenerative hair follicle germ provided with a guide, the guide can be fixed to the target site using a tape or band for skin-bonding, or the like so that the guide does not fall out.

After the continuity between the recipient-side epithelial cells and the epithelial cell-derived side of the regenerative hair follicle germ has been secured some time after transplantation of the regenerative hair follicle germ, the guide can be removed from the transplant site. The timing for removal of the guide can be appropriately set, and for example, the guide is preferably removed from the transplant site 3 to 7 days after transplant. Alternatively, the guide can also be left so that it naturally falls out from the transplant site. A guide of a bioabsorbable material can be left to naturally fall out from the transplant site or until it decomposes or is absorbed.

In this way, by equipping the regenerative hair follicle germ for transplantation with a guide, the recipient-side epithelial cells elongate toward the inside of the transplant site along the guide so as to eliminate foreign substances, while the epithelial cell-derived cells of the regenerative hair follicle germ elongate along the guide. Thereby, the continuity between the recipient-side epithelial cells and the epithelial cell side of the regenerative hair follicle germ after transplantation can be improved. It is also preferable to insert a guide because the maintenance of the polarity of the epithelial cells and the mesenchymal cells can be improved in the regenerative hair follicle germ during culture. Thereby, the efficiency of hair follicle formation can be increased and the orientation during transplantation can be facilitated. In particular, when using a guide in a regenerative hair follicle germ, the hair follicle formation can be stimulated in an intended direction because the continuity between the regenerative hair follicle germ and the recipient-side epithelial cells can be secured. As a result, the hair growth rate from the regenerative hair follicle germ can be improved and it is also possible to control the hair growth direction.

The terms used in the present specification are used to explain the specific embodiments described herein, and are not intended to limit the present invention.

The terms "comprise/include/contain" used in the present specification are intended to mean that the matters as described (members, steps, elements, numbers, etc.) exist except when another understanding thereof is explicit from the context, and such terms do not exclude the existence of other matters (members, steps, elements, numbers, etc.).

Unless a different definition is given, all of the terms used herein (including technical terms and scientific terms) have the same meaning as those widely understood by those skilled in the art in the technical field to which the present invention belongs. Unless a different definition is explicitly given, the terms used herein should be interpreted with a meaning that is consistent with the meaning in the present specification and the related technical field, and they should not be idealized nor interpreted with an excessively formal meaning.

Some of the embodiments of the present invention have been explained referring to schematic diagrams, but the schematic diagrams may be exaggerated in order to clarify the explanation.

The terms "first", "second", and the like are used to express various elements herein, but it is understood that these elements are not intended to be limited by such terms. These terms are used only to distinguish one element from another element, and, for example, the element labeled as "first" can be labeled as "second" and similarly, the element labeled as "second" can be labeled as "first" without departing from the scope of the present invention.

In addition, in the present specification, regarding the expressions "above" or "below/lower/bottom" in the hair follicle, for convenience, in the structure of a hair follicle, "below/lower/bottom" indicates a portion in which the hair papilla exists, and "above" indicates the opposite side of the hair papilla in the hair follicle, or in other words a direction in which hair grows/elongates.

The present invention will now be explained in further detail below referring to Examples. However, the present invention can be embodied by various aspects and should not be construed as limited to the Examples described herein.

EXAMPLES

1. Materials and Methods
(1) Experimental Animals

Hair follicles were collected from a C57BL/6 mouse (CLEA Japan) and a C57BL/6 6-TgN (act-EGFP) mouse at 7 to 8 weeks of age. Also, the regenerative hair follicle genii produced by the experimental method described below was transplanted into a Balb/c nu/nu mouse (SLC) at 6 to 8 weeks of age. The animal care and experimentation was conducted under the approval of the Animal Experimentation Ethics Board of Tokyo University of Science in compliance with the related laws, ministerial ordinances, and guidelines.

(2) Hair Papilla Cell Culture

After euthanizing a C57BL/6 mouse at 7 to 8 weeks of age by cervical dislocation, all layers of the buccal skin and the subcutaneous tissues were collected so as not to damage the hair bulbs. After removal of the subcutaneous tissues surrounding the side-whiskers, the hair follicles were isolated. A side-whisker hair follicle in growth stages I to IV was selected from the isolated hair follicles, and the collagen sheath was removed from the selected side-whisker hair follicle using a 25G injection needle to expose the hair follicle. Next, the hair bulb was isolated from the exposed hair follicle to extract the hair papilla. As a preservation solution for preserving the isolated hair follicle and the extracted hair papilla during the procedure, a DMEM medium (DMEM10) containing 10 mM of HEPES, 10% fetal bovine serum, and 1% penicillin-streptomycin solution was used. The isolated hair papilla was seeded onto a 3.5 cm culture plastic dish (Nippon Becton Dickinson), and primary culture was conducted in an environment of 5% $CO_2$, 37° C., and 95% humidity in DMEM10 containing 10 ng/ml of FGF2 (Wako Pure Chemical Industries, Ltd.). After culturing for 9 days while exchanging the medium on the $4^{th}$ and $8^{th}$ day, the primary cultured hair papilla cells were used to produce a regenerative hair follicle germ. The primary cultured hair papilla cells after the 9-day culture were washed 3 times with PBS (−), ablated with 10 mM EDTA (GIBCO) solution containing 0.05% trypsin, trypsin-neutralized in DMEM10, sufficiently washed, and then preserved under ice until time for use.

(3) Acquisition of Hair Follicle Bulge Epithelial Cells

From the hair follicle of the side-whisker tissue isolated in (2) above, the collagen sheath was removed using a 25G injection needle to isolate the bulge region. The bulge region tissue was reacted for four minutes at 37° C. in a solution of Dispase II having a final concentration of 4.8 U/ml (Becton Dickinson) and 100 U/ml Collagenase (Worthington, Lakewood, N.J.). Subsequently, the bulge region tissue was surgically separated into a bulge region epithelial tissue and a mesenchymal tissue around the bulge using a 25G injection needle. The isolated bulge region epithelial tissue was subjected to a 1-hour enzyme treatment in an incubator with 0.05% Trypsin (Invitrogen, Carlsbad, US), and then passed through a 35 μm pore cell strainer to obtain unified cells.

Further, immediately before producing the regenerative hair follicle germ, the cultured hair papilla cells were collected with 0.05% Trypsin (Invitrogen, Carlsbad, US), and then passed through a 35 μm pore cell strainer to obtain unified cells.

(4) Production of Regenerative Hair Follicle Germ

A regenerative hair follicle germ was produced in accordance with the organ germ method. The detailed procedures were as follows. The unified bulge region cells and the unified cultured hair papilla cells obtained as described above were individually transferred into 1.5 ml microtubes (Eppendorf) coated with silicone grease, and then centrifuged. A supernatant in the culture solution after centrifugation was completely removed using GELoader Tip 0.5-20 ml (Eppendorf) in order to collect the unified bulge region cells or the unified cultured hair papilla cells that had precipitated due to centrifugation. Next, a collagen gel drop was prepared by dropping 30 ml of Cellmatrix type I-A (Nitta Gelatin, Osaka, Japan) onto a petri dish coated with silicone grease (Dow Corning Toray). Approximately 0.2 ml of the unified cultured hair papilla cells prepared as described above were injected into the collagen gel drop using a 0.1 to 10 ml pipette tip (Quality Scientific Plastics) to produce a cell aggregate. Next, approximately 0.2 ml of the bulge region cells prepared as described above were injected into the same gel drop using a 0.1 to 10 ml pipette tip (Quality Scientific Plastics) so as to closely contact the cultured hair papilla cell aggregate, thereby producing a cell aggregate of the cultured hair papilla cells and the bulge region cells. Further, a nylon thread (Matsuda Medical Industry) with a total length of 5 mm was inserted from the bulge region cells of the cell aggregate. Subsequently, the gel drop was left to stand for 5 minutes at 37° C. to solidify it and thereby it strengthens the link between the bulge region cells and the cultured hair papilla cells, and the regenerative hair follicle germ was accordingly produced.

As described below in (5) and (6), subbulge region cells and hair matrix base cells were prepared and used in the production of the regenerative hair follicle germ.

(5) Preparation of Subbulge Region Cells

Using the same procedure as described above in (3) for the acquisition of the bulge region, a constant region above the ringwurst attachment site was isolated from a side-whisker hair follicle of a C57BL/6 mouse at 7 to 8 weeks of age, and a bottommost end of the constant part that is adjacent to the bulge region was isolated as the subbulge region. Subsequently, unified subbulge region cells were obtained using an enzyme treatment and a filter for cell segregation.

(6) Preparation of Hair Matrix Base Cells

The collagen sheath and the dermal root sheath were removed from the hair bulb of the hair follicle of the side-whisker tissue from a C57BL/6 mouse at 7 to 8 weeks of age that was isolated in (2) above, so as to isolate the hair matrix base tissue that is adjacent to the base of the hair papilla using a 25G injection needle. The isolated hair matrix base tissue was treated for 10 minutes at 37° C. with 0.25% trypsin, washed with DMEM10, and then passed through a 35 μm pore cell strainer to obtain unified hair matrix base cells.

In the method for producing a regenerative hair follicle germ described above in (4), when concentrating the unified bulge region cells by centrifugation, approximately 400 of the unified subbulge region cells or approximately 400 of the unified hair matrix base cells obtained as described above in (6) or (7) were mixed with approximately 10,000 of the bulge region epithelial cells and then centrifuged, thereby producing a cell aggregate including the unified subbulge region cells or the unified hair matrix base cells and the unified bulge region cells. The cell aggregate obtained in this way was injected into the gel drop instead of the bulge region cells so as to closely contact the top of the cell aggregate of the cultured hair papilla cells within the gel drop. Thereby, a regenerative hair follicle germ was obtained as a subbulge region cell addition group or a hair matrix base cell addition group.

Each regenerative hair follicle germ produced within a gel by the methods described above was transferred together with the collagen gel onto a 0.4 ml pore size Cell Culture Insert (Becton Dickinson) in which a 6-well plate (Becton Dickinson) to which 1 ml of DMEM10 was added had been set, and then subjected to culture for 2 days under conditions of 37° C., 5% $CO_2$, and 95% humidity.

(8) Transplantation of Regenerative Hair Follicle Genii into Nude Mouse Skin

A nude mouse was anesthetized with pentobarbital in accordance with a conventional method, and it was placed in a natural recumbent position after disinfecting its back with isodine. The mouse was punctured using a V-lance micro scalpel (Alcon Japan) to form a graft wound from the skin epidermal layer to the lower layer portion of the dermal layer. The graft wound extended from the body surface to a depth of up to 400 µm in the vertical direction and about 1 mm in the horizontal direction. The collagen gel was removed from the regenerative hair follicle germ into which a guide made of nylon thread was inserted, and the regenerative hair follicle germ was inserted so that the epithelial cell component was facing the body surface side of the graft wound. The transplant depth was adjusted so that the top end of the epithelial cell component of the regenerative hair follicle germ was exposed at the top end of the graft wound, and the regenerative hair follicle germ was positioned so that the nylon thread guide was exposed at the body surface. The nylon thread guide was fixed with a Steritest strip (3M) to the skin surface near the graft wound, and then the graft wound was protected with Nurseban and Surgical Tape (3M). The protective tape was removed 5 to 7 days after transplantation, and then the transplant site was observed over time after the adherence of the transplant had been determined visually or with a fluorescence stereomicroscope.

(9) Hair Growth Observation Over Time and Histological Analysis

The transplant site of the regenerative hair follicle germ was observed visually and under a fluorescence stereomicroscope to evaluate the hair growth.

Figure 2:
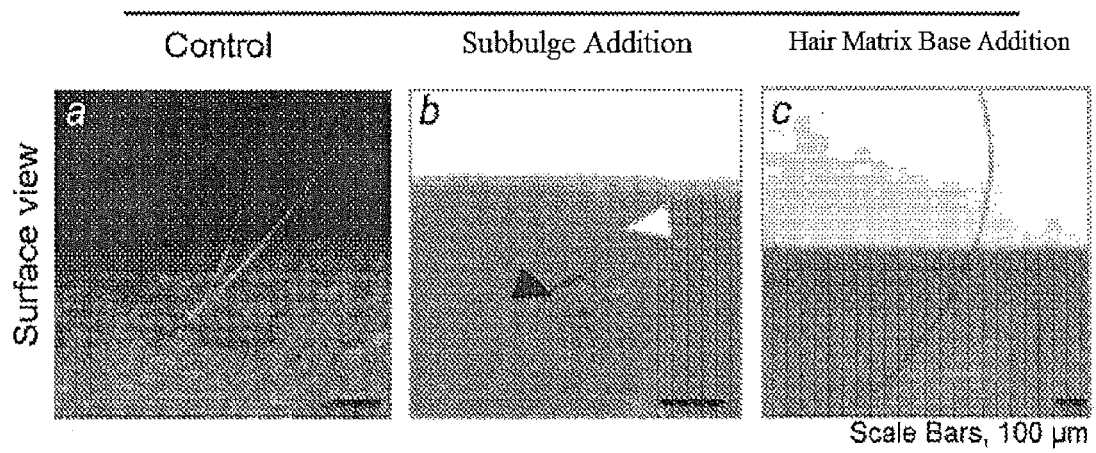
FIG. 2 shows photos captured by a stereoscopic microscope depicting a transplant site in which a hair follicle has regenerated and hair has grown after transplantation of a regenerative hair follicle germ produced under the following three conditions (FIGS. 2a to 2c).

2. Results (1) Hair Color in Regeneration of Body Hair and Whiskers By Intracutaneous Transplant of Regenerative Hair Follicle Germ The whiskers that were regenerated by transplantation of the regenerative hair follicle germ produced from the bulge region and the hair papilla cells derived from an adult mouse side-whisker of a colored mouse were white at a frequency of 95.5% (FIG. 2a). As shown in FIG. 1, it is known that the pigment stem cells that control hair color by melanin pigmentation in the hair shaft are distributed in the subbulge region below the bulge region. In addition, melanocyte precursor cells are also distributed in the hair matrix base of the hair bulb, and differentiate into melanocytes within the hair matrix to color the hair shaft. The regenerative hair follicle germ derived from an adult side-whisker was confined to the bulge region which does not include melanoblasts to construct the regenerative hair follicle germ, and thus the regenerative hair follicle germ did not have melanoblasts, and it was suggested that the regenerative hair may become white because the hair matrix of the regenerated hair follicle does not contain any differentiated melanocytes.

(2) Hair Color Control by Addition of Pigment Stem Cells

An examination was conducted regarding whether the hair color of a regenerative hair was affected when unified cells were obtained from the subbulge region in which colored hair melanoblasts exist and the hair matrix base region in which melanocyte precursor cells are distributed in an adult mouse side-whisker hair follicle, respectively, and then the unified cells were added to a cell mass that constitutes a regenerative hair follicle germ. Upon analyzing the color and properties of a hair shaft that grew at three weeks after intracutaneous transplantation of the regenerative hair follicle germ, regenerative black-colored hair was successfully obtained in both segments in which the subbulge region or the hair matrix base cells were added (black arrow mark in FIG. 2b and FIG. 2c).

Figure 3:
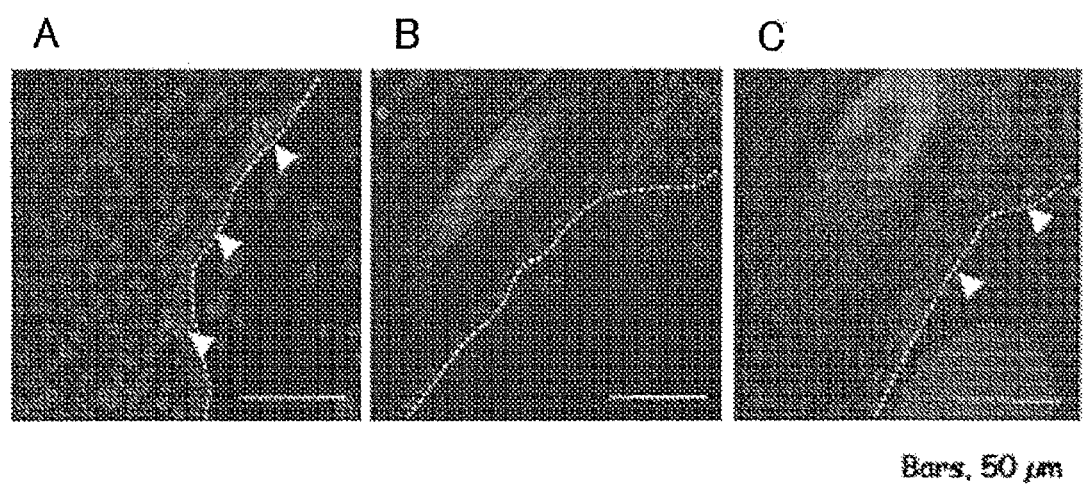
FIG. 3 shows the results upon in situ hybridization of dopachrome tautomerase (Dct), which is a melanoblast differentiation lineage marker, in an external root sheath of the subbulge region, which is an area in which a melanoblast stem cell niche exists, of a natural hair follicle or a hair follicle that was regenerated by transplantation of a regenerative hair follicle germ. The images in FIG. 3 were captured with a fluorescent microscope after in situ hybridization.

Herein, in order to confirm whether a melanoblast stem cell niche is formed in a hair follicle that was regenerated from a regenerative hair follicle germ and that formed black hair as similar to that of a natural hair follicle, in situ hybridization of dopachrome tautomerase (Dct), which is a melanoblast differentiation lineage marker, was carried out. As a result, in a hair follicle that was derived from a regenerative hair follicle germ produced by adding unified cells of the subbulge region to a cell mass of bulge region and hair papilla cells derived from a colored adult mouse side-whisker and that formed black hair, melanoblasts were detected in an external root sheath of the subbulge region, which is a location at which a melanoblast stem cell niche should exist, as similar to that of a natural hair follicle. This demonstrates that a hair follicle regenerated from a regenerative hair follicle germ produced by adding unified cells of the subbulge region forms a melanoblast stem cell niche and melanoblasts are appropriately stored. On the other hand, in a hair follicle that was regenerated from a regenerative hair follicle germ produced from the bulge region and hair papilla cells derived from a colored adult mouse side-whisker and that formed white hair, melanoblasts were not detected in a location at which a melanoblast stem cell niche should exist (FIG. 3).

Figure 4:
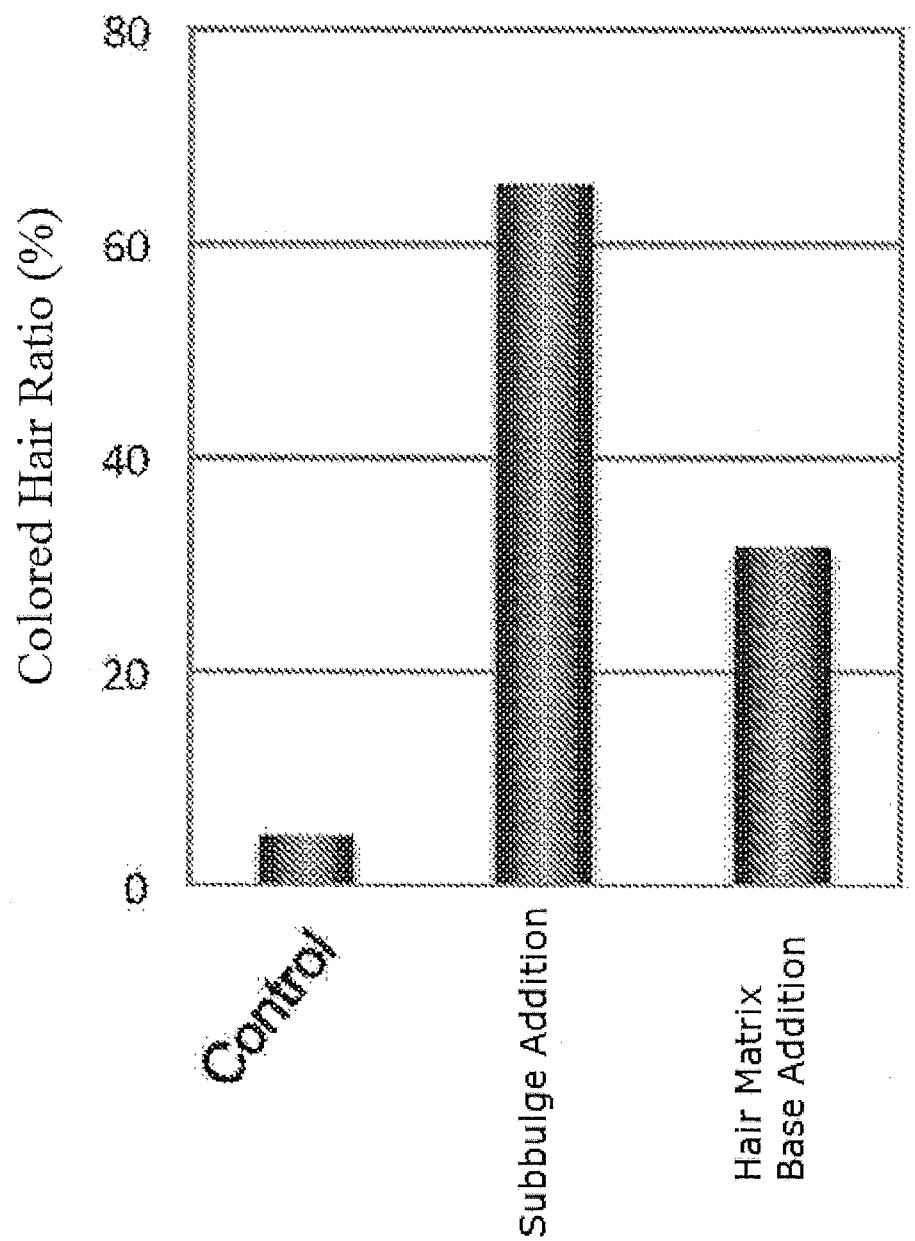
FIG. 4 respectively illustrates the colored hair ratio of hair that grows first after transplantation of a regenerative hair follicle germ produced from adult mouse side whisker-derived bulge region epithelial cells and adult mouse side whisker-derived hair papilla cells (control), a regenerative hair follicle germ produced by further adding adult mouse side whisker-derived subbulge region cells to adult mouse side whisker-derived bulge region epithelial cells and adult mouse side whisker-derived hair papilla cells (subbulge addition segment), and a regenerative hair follicle germ produced by further adding cells collected from an adult mouse side whisker-derived hair matrix base to adult mouse side whisker-derived bulge region epithelial cells and adult mouse side whisker-derived hair papilla cells (hair matrix base addition segment).
Figure 5:
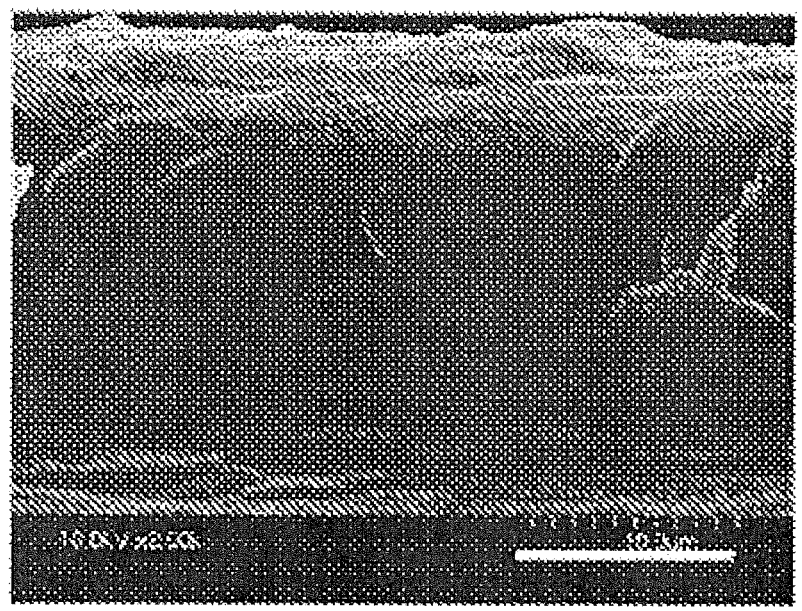
FIG. 5 shows the results upon observation under an electron microscope of a hair shaft of a hair grown from a hair follicle that was regenerated by transplantation of a regenerative hair follicle germ produced using adult mouse side whisker-derived bulge region epithelial cells, adult mouse side whisker-derived hair papilla cells, and cells collected from an adult mouse side whisker-derived hair matrix base into the skin of a recipient mouse.

Also, the frequency of changes in hair color depending on whether or not subbulge region cells or hair matrix base cells were added was measured. As a result, in the subbulge region cell addition group, 65.4% of the hair was colored, and the rate of black hair was 14.5 times higher than the control which used bulge region cells alone as the epithelial cells (FIG. 4). Similarly, in the hair matrix base cell addition group, 31.6% of the hair was black, and the rate of black hair was 7.0 times higher than the control which used bulge region cells alone (FIG. 4). In addition, upon collecting hair that grew from a regenerative hair follicle germ produced by adding hair matrix base cells and then analyzing the morphology of the surface of the hair shaft under a scanning electron microscope, it was observed that a cuticle structure similar to that of natural hair had developed (FIG. 5).

Herein, in order to confirm whether the melanoblast stem cell niche replicates the stem cell maintenance function such that the hair follicle can permanently form black hair in a regenerated hair follicle that produces black hair, the black hair formation capability in a regenerated hair follicle after a long period of time had elapsed since transplantation was observed. As the regenerative hair follicle germ used for observation, a regenerative hair follicle germ produced by adding unified cells derived from the hair matrix base region to colored adult mouse side-whisker-derived bulge region epithelial cells and adult mouse side-whisker-derived hair papilla cells (hair matrix base addition segment) was used. As a control segment, a hair follicle regenerated by transplantation of a regenerative hair follicle germ produced from colored adult mouse side-whisker-derived bulge region epithelial cells and adult mouse side-whisker-derived hair papilla cells was observed.

Figure 6:
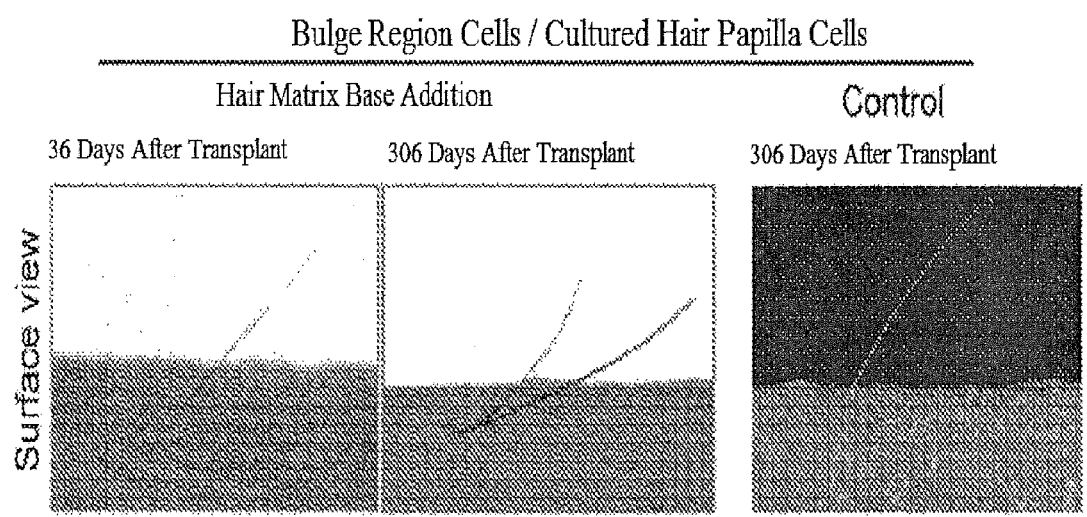
FIG. 6 shows photos captured by a stereoscopic microscope depicting a transplant site at which hair has grown 36 days after transplantation and 306 days after transplantation of a regenerative hair follicle germ produced under the following two conditions. The left and middle images in FIG. 6 show a hair growth site 36 days after transplantation and 306 days after transplantation of a regenerative hair follicle germ produced by further adding cells collected from an adult mouse side whisker-derived hair matrix base to adult mouse side whisker-derived bulge region epithelial cells and adult mouse side whisker-derived hair papilla cells (hair matrix base addition segment). Also, the right image in FIG. 6 shows a hair growth site 306 days after transplantation of a regenerative hair follicle germ produced from adult mouse side whisker-derived bulge region epithelial cells and adult mouse side whisker-derived hair papilla cells (control).

As a result, in the hair matrix base addition segment, it was confirmed that black hair was formed 36 days and 306 days after transplantation of the regenerative hair follicle germ (FIG. 6). In this test, in the hair follicle formed from the regenerative hair follicle germ, one hair cycle lasted on average about 15 days, and thus it was confirmed that formation of black hair was repeated on average about 20 times. On the other hand, in the control segment, only white hair was confirmed even 306 days after transplantation.

From the above results, it was demonstrated that it is possible to control hair color by adding cells of a region that includes melanoblasts or melanocyte precursor cells to a regenerative hair follicle germ. Also, it was demonstrated that colored hair generated by a regenerative hair follicle germ produced by adding pigment stem cells has a hair shaft with normal morphology.

Further, it was demonstrated that a hair follicle regenerated from a regenerative hair follicle germ produced by adding pigment stem cells is able to regenerate a melanoblast stem cell niche in the hair follicle. In addition, it was demonstrated that a hair follicle regenerated from a regenerative hair follicle germ produced by adding pigment stem cells can permanently maintain the formation of colored hair. This demonstrates that melanoblasts can be maintained over a long period of time in a melanoblast stem cell niche within a regenerated hair follicle, and that the physiological function of a hair follicle can be replicated so as to supply melanocytes to the hair matrix.

The invention claimed is:

1. A method for producing a regenerative hair follicle genii for transplantation in which a color of hair that grows after transplantation is controlled, comprising:
   preparing a first cell mass comprising mesenchymal cells,
   preparing a second cell mass comprising epithelial cells,
   preparing a cell mass comprising pigment stem cells,
   binding the cell mass comprising the pigment stem cells to at least one among the first cell mass and the second cell mass, and
   subsequently closely contacting the first cell mass and the second cell mass, at least one of which has been bound to the cell mass comprising the pigment stem cells, and culturing them within a support.

2. The method according to claim 1, wherein the first cell mass substantially consists of mesenchymal cells.

3. The method according to claim 2, wherein the cell mass comprising the pigment stem cells is subjected to a unification treatment.

4. The method according to claim 2, wherein the pigment stem cells are subbulge region-derived melanoblasts or hair matrix base-derived melanocyte precursor cells.

5. The method according to claim 1, wherein the second cell mass substantially consists of epithelial cells.

6. The method according to claim 5, wherein the cell mass comprising the pigment stem cells is subjected to a unification treatment.

7. The method according to claim 5, wherein the pigment stem cells are subbulge region-derived melanoblasts or hair matrix base-derived melanocyte precursor cells.

8. The method according to claim 1, wherein the cell mass comprising the pigment stem cells is subjected to a unification treatment.

9. The method according to claim 8, wherein the pigment stem cells are subbulge region-derived melanoblasts or hair matrix base-derived melanocyte precursor cells.

10. The method according to claim 1, wherein the pigment stem cells are subbulge region-derived melanoblasts or hair matrix base-derived melanocyte precursor cells.

11. The method according to claim 1, wherein the pigment stem cells are hair matrix base-derived melanocyte precursor cells.

12. The method according to claim 1, wherein when binding the cell masses together, the ratio of the number of cells in the first cell mass or the number of cells in the second cell mass relative to the number of cells in the cell mass comprising the pigment stem cells is within a range of 0.1:1 to 100:1.

13. The method according to claim 1, wherein when closely contacting the first cell mass and the second cell mass and culturing them in the support, the ratio of the number of cells in the first cell mass relative to the number of cells in the second cell mass is within a range of 0.3:1 to 1:1.

14. The method according to claim 1, wherein the mesenchymal cells are hair papilla cells or dermal root sheath cells.

15. The method according to claim 1, wherein the epithelial cells are bulge region epithelial cells or hair matrix basal epithelial cells.

16. The method according to claim 1, wherein the mesenchymal cells or the epithelial cells are derived from an adult hair follicle.

17. The method according to claim 1, wherein the method further comprises inserting a guide into the regenerative hair follicle germ.

* * * * *